United States Patent [19]

Bacchi et al.

[11] Patent Number: 5,285,657
[45] Date of Patent: Feb. 15, 1994

[54] CONTROLLED-ENVIRONMENT MEDICAL CONTAINER

[75] Inventors: Bernard Bacchi, Garches; Patrick Marchot, Colombes; Philippe Mauriat, Vanves; Gilles Touati, Tours; Philippe Pouard, Clamart; Alain Magnard, Longpont sur Orge; Philippe Thomas, Villiers sur Orge; Daniel Thépaut, Villeconin, all of France; Fernand Muller, Vianden, Luxembourg

[73] Assignee: Electrolux S.A.R.L., Vianden, Luxembourg

[21] Appl. No.: 766,273

[22] Filed: Sep. 27, 1991

[30] Foreign Application Priority Data

Sep. 28, 1990 [FR] France .................. 90 12022

[51] Int. Cl.$^5$ .............................................. F25D 3/08
[52] U.S. Cl. ................................ 62/457.9; 62/457.7; 62/371; 435/1
[58] Field of Search .............. 62/457.1, 457.7, 457.9, 62/3.62, 371, 3.61, 3.6; 435/1

[56] References Cited

U.S. PATENT DOCUMENTS 4,186,565 2/1980 Toledo-Pereyra .
4,326,383 4/1982 Reed et al. .................... 62/3.62
4,745,759 5/1988 Bauer et al. .

FOREIGN PATENT DOCUMENTS 0336791 10/1989 European Pat. Off. .
0376763 7/1990 European Pat. Off. .

OTHER PUBLICATIONS

Medizintechnik, vol. 23, No. 1, 1983, Berlin, pp. 2-5, Von Dietmar Scholz, et al., "Organkonservierungsmaschine OKM 82".
Ninth Annual Conference of the IEEE Engineering in Medicine and Biology Society, Boston, Mass., Nov. 13-16, 1987; pp. 24-25, N. Chauveau, et al., "Experimental Heart Preservation System".

Primary Examiner—John M. Sollecito
Attorney, Agent, or Firm—Oblon, Spivak, McClelland, Maier & Neustadt

[57] ABSTRACT

The container with a thermally insulated enclosure (100) is equipped with a refrigerating unit (20), with a pumping unit (30), with a control unit and with an electrical power source. This container also comprises a disposable aseptic detachable transporting assembly (60) together with a reservoir bag for a physiological fluid, a collector bag for gathering this fluid, a vessel for transporting an organ with a device for suspending the organ, a fluid dispensing element and pipework (66) for connecting this reservoir bag, dispensing element, vessel and collector bag by passing via the pumping unit. Application for the preservation and transporting of live organs to be transplanted.

12 Claims, 4 Drawing Sheets

CONTROLLED-ENVIRONMENT MEDICAL CONTAINER

The present invention relates to the medical field and, in particular, to medical equipment and, more especially, relates to a controlled-environment container for the preservation and the transporting of live organs to be transplanted.

As is known, in the medical field a technique currently used today consists in grafting complete organs when all other treatments have proved to be ineffective in order to overcome pathological anomalies or functional disorders.

This technique makes use of a donor from whom an organ or group of organs is removed and a recipient to whom the organ or group of organs thus removed is grafted in order to substitute for a failing one which previously was ablated.

Nowadays this type of intervention is conventional for heart, liver and kidney transplants, even for combined heart-lung transplants.

The medical teams responsible for the removing and those responsible for the grafting, use protocols, of which there exist in general diverse schools together with variations. Of course, it is necessary that the removing and grafting protocols should be similar and be compatible.

It is not very common that the donor and the receiver are simultaneously close in time and geographically. This is why it is essential to preserve and most often to transport the organ between its removal and its reimplantation.

After removal, it is necessary to check the actual state of the organ and to ensure also that the organ is preserved under good conditions before its reimplantation, and it is essential also to ensure that, before proceeding to the latter, the state of histological and functional preservation is correct in order to ensure a reasonably high probability that the graft will take with the maximum chance of success.

The techniques for preserving an organ during the transporting phase are numerous, and also depend on the removal and reimplantation protocols. Thus in heart transplants it has been proposed first of all to stop the heart before removal by injection with a cold cardioplegia solution at approximately 4° C. and then subsequently to preserve the graft cold by immersing it in a Collins solution and/or carrying out a hypothermal intracoronary continuous perfusion of a Fluosol solution, whilst seeing to it that the temperature of preservation is not close to 0° C. in order to prevent deleterious effects for the myocardium which result in cryolesions.

The state which the organ is in at the moment of its reimplantation must also be checked. It is easily imagined that this state is not only a function of the initial state at the moment of the removal but also depends on the conditions of preservation and of transporting. It is therefore absolutely essential that the medical team responsible for the grafting be able to have at their disposal and understand the maximum amount of information pertaining to the organ, to the actual removal as well as the conditions in which the transporting was effected. This information, added to that obtained directly by examinations and analyses of the organ just before its reimplantation make it possible to determine whether the state in which the organ is received justifies the recipient being "prepared" for receiving the grafting of this organ. This information is, for example, that which results especially from histological studies and birefringence measurements on myocardial biopsies and on measurements of the intramyocardial pH with the help of a probe.

The transporting conditions are numerous and varied. Depending on the location, the external ambient temperatures may be considered, more or less, as being between approximately −20° C. and +50° C. The transporting means may involve ships, lorries, ambulances, cars, motorbikes, aeroplanes and helicopters which have their own regimes of shock and vibration with specific amplitudes and frequencies.

The complexity and the variety of these techniques for removal, transporting and implantation, as well as the successes of the grafts thus made, are greatly dependent on the suitability of the technique for preserving and transporting the organ.

It can be appreciated therefore that there is great importance and significance in being able to have a container which allows a removed organ to be preserved and transported, whilst being capable of easily adapting, at will, to the protocols effectively chosen by the medical teams, and which may also enable the latter to have at their disposal the maximum amount of information pertaining to the preservation and transporting conditions of the organ, between its removal and its grafting.

A container for the transporting of kidneys is described by the document U.S. Pat. No. 4,745,759. This document discloses a specialised container for the preservation of kidneys which, although giving relative satisfaction for these organs, is only suitable for this type of organ and does not lend itself at all for adaptation to the choices of operating and preservation protocols, nor, further, does it make it possible to know under what conditions the organ has been preserved and transported. This container has no scope for universality.

The object of the invention is to remedy for the most part the drawbacks of the prior art and to make it possible to preserve and transport living organs to be transplanted under chosen conditions, at will, according to the decisions of the medical teams, and the progress of which may be precisely known at any moment in order to facilitate diagnosing the state of the organ received just before its possible grafting.

The subject of the invention is a controlled-environment container for preserving and transporting living organs to be transplanted which is formed, inter alia, by a box with d hinged lid delimiting a thermally insulated inner enclosure and outer compartments, by a refrigerating unit which is housed partly in one of these compartments and partly in this enclosure and which is intended for maintaining a selected specified temperature in this enclosure, by a pumping unit which is housed partly in another of these compartments and partly in this enclosure and which is intended for supplying at least one organ placed in this enclosure with a fluid for physiological use at a selected specified pressure and flow rate, by a control unit which is connected to these refrigerating and pumping units and which is intended for operating them and for monitoring their assigned operations and by an electrical power source which is connected to these refrigerating and pumping units and to this control unit and which is intended for powering them. This container is especially noteworthy in that it comprises a disposable aseptic detachable transporting assembly provided, inter alia, with a reservoir bag intended for containing this fluid for supplying this organ, with a collector bag intended for collecting this liquid which has supplied this organ, with a transporting vessel for receiving this organ and intended for being equipped with a suspension device in order to hold this organ and with a dispensing element for supplying the organ with this fluid, and also with pipework connecting this bag reservoir bag and this dispensing element by passing via the pumping unit and connecting this vessel and this collector bag.

Other features of the invention will emerge from reading the description and the claims which follow together with examination of the attached drawing, given solely by way of example, where:

Figure 1:
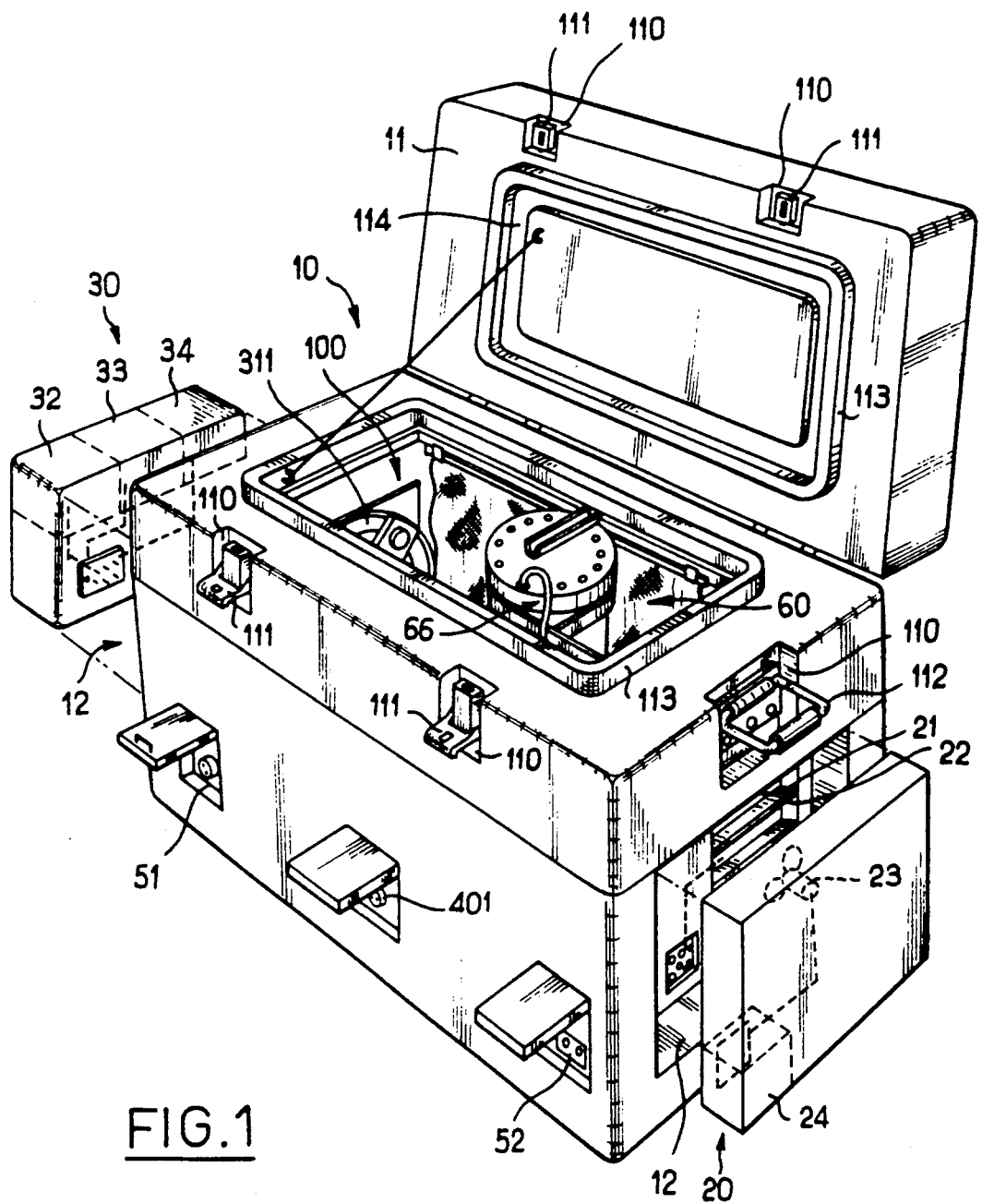
FIG. 1 is a diagrammatic overall view, in perspective, of a container according to the invention.
Figure 2:
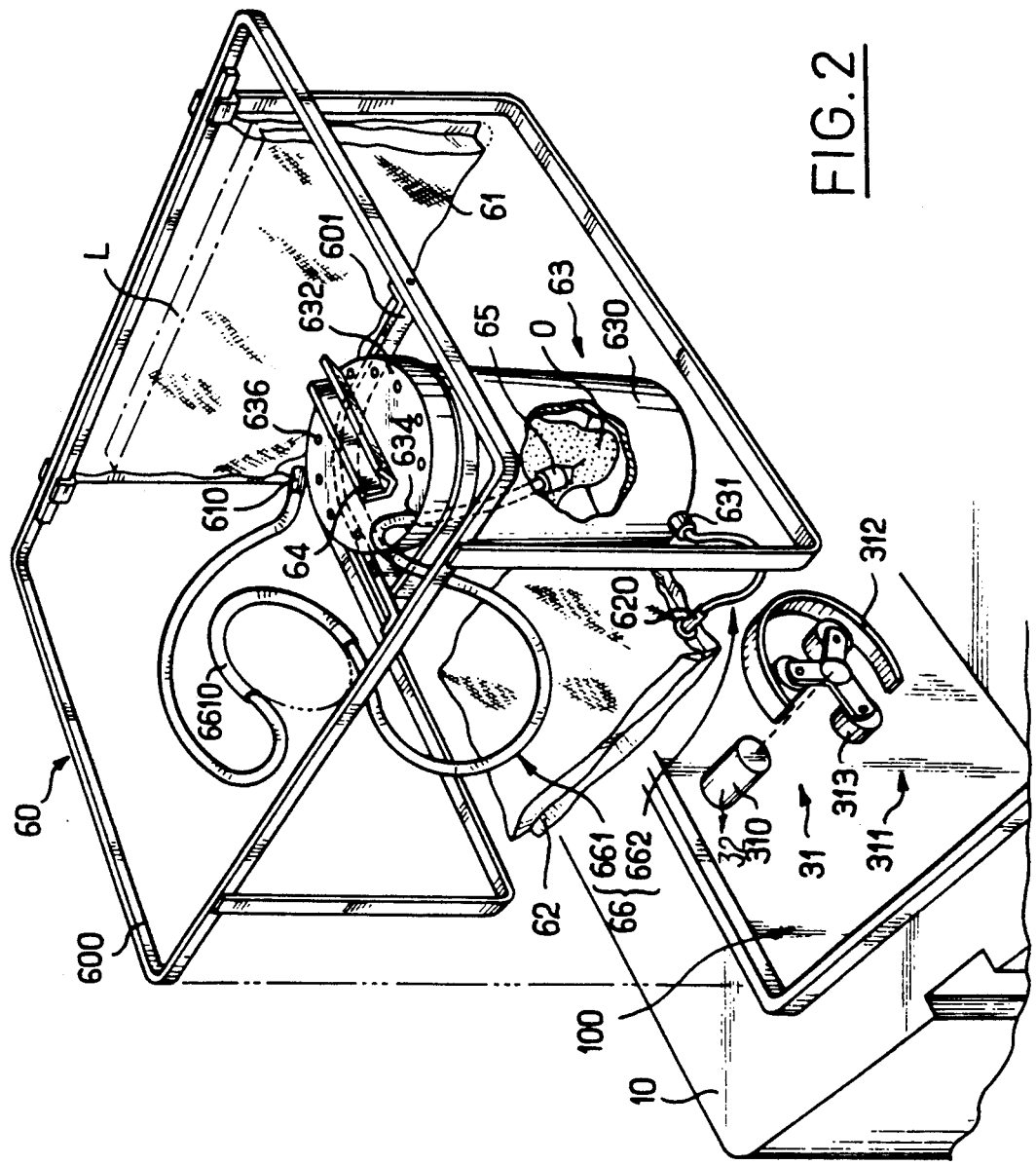
FIG. 2 is a view, in perspective, of the detachable transporting assembly and of a portion of the box.
Figure 3:
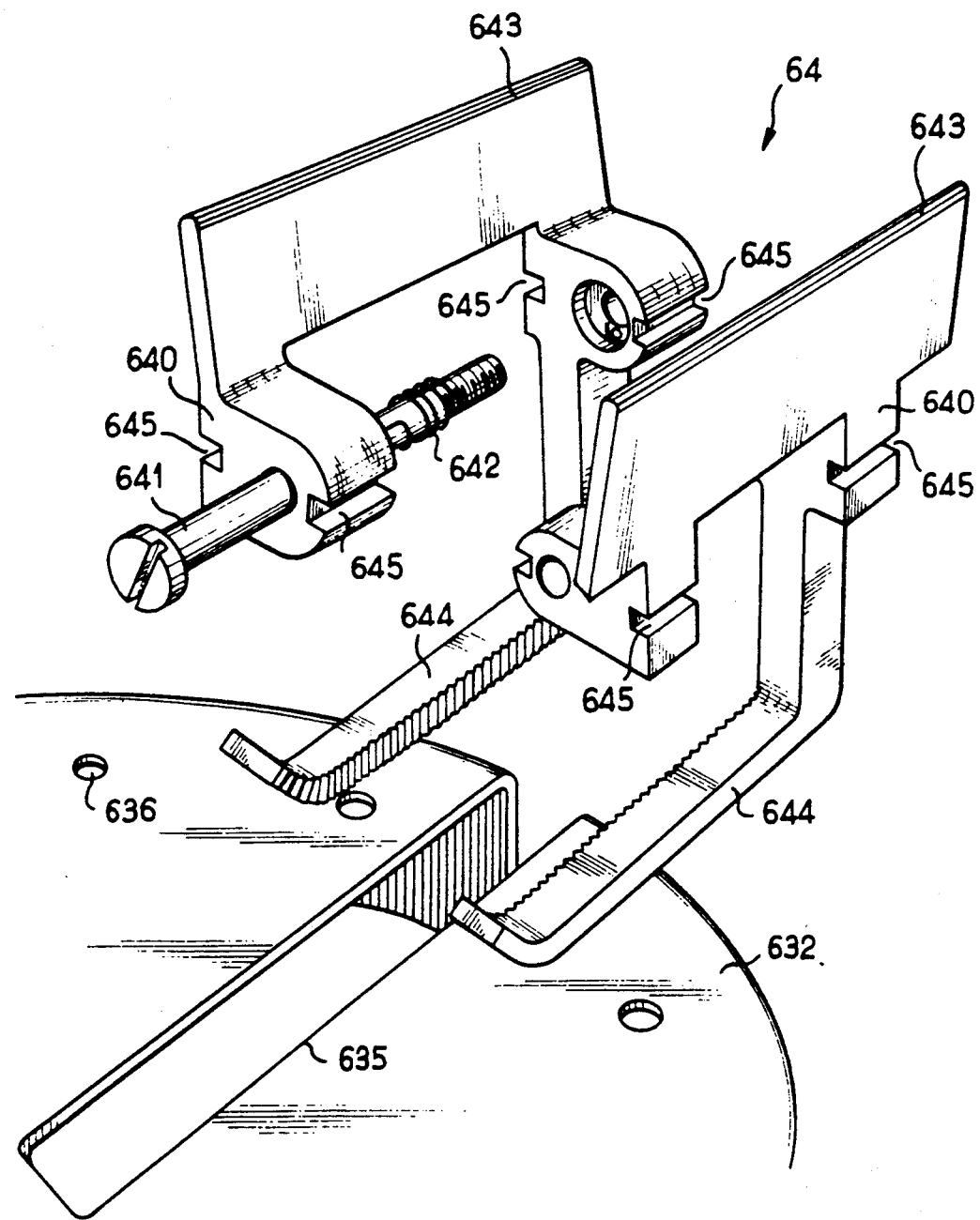
FIG. 3 illustrates a portion of the transporting vessel and an embodiment of the suspension device in exploded view; and, FIG. 4 is a block diagram illustrating the functional connections between various constituents of the container according to the invention.
Figure 4:
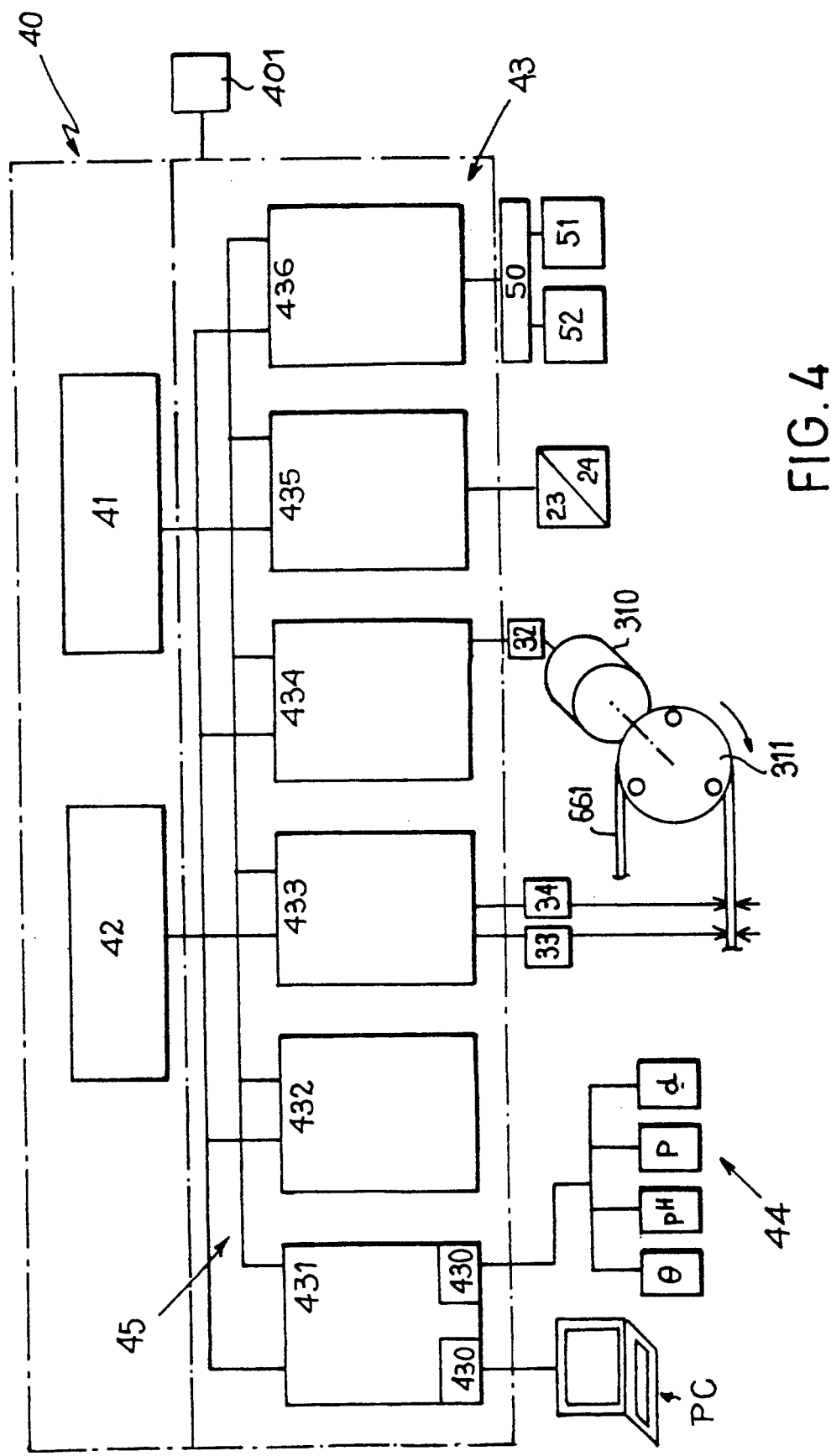

The containers for preserving and/or transporting living organs or tissues are well known in the technical field and there will only be described hereinbelow that which relates directly or indirectly to the invention. For the rest, the skilled man of the technical sector concerned will draw on current conventional solutions at his disposal for addressing particular problems with which he is confronted.

Throughout the following one and the same reference number will be used for identifying an equivalent element, regardless of the embodiment.

For the convenience of this specification there will be described in succession each of the constituents of a controlled-environment container for preserving and transporting living organs to be transplanted according to the invention.

As is seen by examining the figures of the drawing, this embodiment of a container according to the invention comprises a box 10, a refrigerating unit 20, a pumping unit 30, a control unit 40, an electric power source 50 and a detachable transporting assembly 60.

The box 10 comprises, essentially, a strong shell made, for example, of metal or synthetic resins with a thermal insulation made of, for example, glass wool or expanded polystyrene providing a good thermal insulation, and to which a hinged lid 11 is fixed. This box is provided with cavities 110 in which are housed clasps 111 and transporting handles 112. of which only one is visible, all of conventional type. Baffles 113 and a gasket 114 provide the sealing between box and lid when the latter is in the closed position, locked by the clasps 111. A small chain or strap or hinged stay, illustrated but not referenced, limits the extent of opening of the lid.

As is seen, the box 10 defines on the outside service compartments 12, for example, two disposed laterally opposite each other to which further reference will be made, and an inner thermally insulated enclosure 100 intended for receiving, inter alia, an organ O to be transplanted.

The refrigerating unit 20 comprises a cryogenic generator 21, preferably absorbing heat by Peltier effect, and a heat exchanger 22. This unit comprises a blower 23, for example a blower having a turbine which enables the atmosphere of the enclosure 100 to be circulated over the heat exchanger 22 in order to fix and maintain the selected inner temperature thereof. This unit comprises a regulating device 24, for example an electronic regulating device, which makes it possible to compare the temperature inside the enclosure with a set value and to control the cryogenic generator 21 and the blower 23 so as to maintain the temperature in the thermally insulated enclosure 100 at the desired set value, within a close tolerance. For reasons explained hereinbelow, this unit is connected to the control unit 40 and to the electrical power supply 50.

This refrigerating unit 20 is housed partly in one of the compartments 12. The remainder of this unit, in particular the heat exchanger 22, the blower 23 and the probe of the regulating device 24 are placed in the enclosure 100.

The pumping unit 30 comprises a pump 31, preferably a peristaltic pump, with a motor 310 and a pump head 311 provided with a guide 312 and a rotor, for example having three rollers 313 preferably having balls, as illustrated. This pumping unit also comprises a control cell 32, a bubble detector 33 and safety devices 34 to which further reference will be made hereinbelow. Preferably this motor is a stepping motor, each step of which is divided into sixteen microsteps.

This pumping unit 30 is housed partly in the other one of the compartments 12. The rest of this unit, in particular the pump head 311 and the probes of these control cell 32, bubble detector 33 and safety devices 34 are placed in the enclosure 100. This pumping unit allows flow rates to be adjusted continuously between 1 ml/h and 300 ml/min approximately at pressures of the order of approximately 10 to 100 mm/Hg, that is 1.33 to 13.3 kPa for example.

This pumping unit is connected to the control unit 40 and to the electric power source 50 for reasons explained hereinbelow.

The control unit 40 essentially comprises an alphanumeric keyboard 41 with function keys, a display screen 42, an electronic circuit 43, sensor-actuators 44 and connections 45. The electronic circuit 43 essentially comprises memories, logic circuits, comparators and instruction files. The sensor-actuators 44 are especially intended for controlling the refrigerating unit 20 and the pumping unit 30, especially by virtue of their probes as will emerge from reading that which follows. This control unit 40 is housed, at least partly, in at least one of the compartments 12. The sensor-actuators 44, in particular, are placed in the enclosure 100. It is clear that this control unit 40 may be housed also in a double bottom or in a double wall, for example at the front and/or at the back, which are provided with a detachable panel in order to gain access thereby, from the inside and/or the outside.

The electronic circuit 43 forms a software management centre and an equipment management and control centre.

The structure of this electronic circuit is such that the software management centre is installed on a personal microcomputer, of the portable type, configured for capturing and storing, that is to say inputting, all the parameters necessary for operating the container and monitoring it throughout the transporting. The functions of this software management centre are, for example, to:

record general information (location of removal, date, hour, identities of the people involved . . . );

record the current temperatures θ, flow rates d, pressures P, pH, . . . ;

record the set values of the temperatures, flow rates, pressure, pH . . . ;

introduce special instructions (different perfusion cycles, changes to the operation of the container depending on certain values encountered for specified parameters . . . );

trace continuously on the screen, preferably graphically and in colour, the change of the parameters;

display and print out the history of the transporting.

This equipment management and control centre comprises:

a "microcomputer" board 431 which is the cornerstone of the assembly;

a "memory" board 432 specific for serving as "Black Box";

a "bubble detector, safety devices" board 433 for monitoring the conditions of the flow of the physiological fluid through the pipework and the presence of the tubing of the latter in the pump head, which board is controlled by the "microcomputer" board;

a "pump" board 434 also controlled by the "microcomputer" board, for adjusting the intensity of the current to the motor 310 driving the pump head 311 so as to fix the driving torque thereof and if necessary also to control it in terms of torque-speed in order to obtain a pressure known to within approximately ±20%;

a "cold" board 435 also controlled by the "microcomputer" board for adjusting the operation of the refrigerating unit;

a "power" board 436 for supplying all the voltages and all the currents necessary for the operation of the container and automatically providing the switching operations after connecting to external power sources.

In order to do this, for example a PC microcomputer of the MOTOROLA 68000 type is used with two standard RS 232 type connections 430 for communicating between the latter and the control electronics associated with the sensor-actuators 44.

In addition, an appropriate socket 401 placed in a suitable location makes it possible optionally to connect to an external computer in order to enable exchange and processing of information.

It goes without saying that visual, acoustic or other type alarms make it possible to indicate in real time or at a later time, any anomaly or deviation with respect to a set value, particularly a serious one.

The electrical power source 50 is intended for supplying the refrigerating unit 20, the pumping unit 30 and the control unit 40. This electrical power source is for example formed by a internal battery such as a Pb or Ni-Cd accumulator which enables the container according to the invention to operate independently in the absence of any connection to external power sources. It also comprises connection sockets 51, 52 and electrical converters, both in terms of frequency and voltage, which make it possible to use external direct current power sources of diverse voltages and alternating current sources of diverse voltages and varied frequencies. These external sources enable the internal power source to be substituted or relayed. This is conventional and no further elaboration of this will be made, there being numerous solutions. It is sufficient to indicate that the container according to the invention is suitable for operating connected to external DC power sources of voltages preferably between, approximately, 5 and 24 V and to external AC power sources of voltages preferably between, approximately, 90 and 270 V and frequencies between, approximately, 50 and 400 Hz.

The detachable transporting assembly 60 is formed, inter alia, by a support holder 600. In this holder are arranged a reservoir bag 61 for physiological fluid L provided with a nozzle 610, a collector bag 62 also provided with a nozzle 620, a vessel 63 for transporting organs with a suspension device. 64 and a dispensing element 65. The pipework 66 makes it possible to connect the nozzle 610 of the reservoir bag 61 to the dispensing element 65 and the transporting vessel 63 to the nozzle 620 of the collector bag 62. The portion of the pipework 66 which serves as pipe 661 for connecting the nozzle 610 of the reservoir bag 61 to the dispensing element 65 comprises a section which forms a tubing 6610 intended for being associated with the pump head 311, between the guide 312 and the rotor 313 and suitable to be periodically deformed by the rollers 313, as is common for a peristaltic pump. As is seen, the guide 312 of circular configuration envelops a portion of the outer circular path of the rollers of the rotor of the pump head. The gap between guide and rollers is intended for receiving the tubing. This tubing is preferably silicone based. All this is shown clearly in the figures of the drawing.

The purpose of the bubble detector 33 is to monitor the quality of the flow of the physiological fluid. The purpose of the safety devices 34 is to permit the operation of the pumping unit only if the tubing has been engaged in the pump head and has been correctly inserted therein. An appropriate suitable device holds the tubing thus installed.

The transporting vessel 63 essentially comprises a body 630 with a nozzle 631 intended for being connected to the portion of the pipework 66 which serves as pipe 62 for connecting the nozzle 631 of the vessel 63 to the nozzle 620 of the collector bag 62. The body 630 is intended for receiving a lid 632 optionally held in place by a fastening of any appropriate type, for example having a screwed joint, elastic fixture, "frog", . . . As is seen in the drawing, this lid 632 has various openings. Among these various openings figures an approximately semi-circular peripheral notch 634 which is intended for the passage of the pipe 661 going to the dispensing element 65. Among these openings also figures an approximately rectangular slot 635 which emerges at the periphery of the lid and which is intended for receiving, preferably by sliding, the suspension device 64. In addition to this notch and this slot, these openings also comprise perforations 636 which are distributed in a circle close to the periphery of the lid, and to which reference will be made further. All this clearly shown in the figures of the drawing.

In the embodiment illustrated, the suspension device 64 is, for example, a kind of gripper. This gripper comprises two arms 640 joined together by a hinge pin 641 in the manner of a scissor blade. A spring 642 tends to hold the gripper closed. The arms 640 are ended at one extremity by gripping ears 643 intended for manually controlling their opening, and at the other extremity by clamping jaws 644 intended for engaging with a portion of the organ to be transported. As is seen, each of these branches is provided with a groove 645 placed in the vicinity of the pin and on the side which is close to the gripping ears. These grooves 645 are intended for engaging in the slot 635. As is seen, when the gripper is thus mounted on the lid it is locked and imprisoned in the closed position. When the lid is subsequently fixed onto the body of the vessel, the gripper is also immobilised in place.

According to an alternative form (not shown) the suspension 64 is, for example, formed by a net, optionally clad with foam or the like, in order to receive the organ to be transplanted which may or may not be also suspended from the gripper referred to hereinabove. This net is then hooked onto the lid by virtue of the perforations 636, in any appropriate manner.

According to an alternative embodiment the body 630 of the vessel 63 may be provided with a lid 632 having multiple partitions which are virtually parallel to each other so as to provide a chamber accessible in the manner similar to that of a case having a double bottom. These partitions end laterally with oppositely disposed rims giving a dish configuration and forming virtually a baffle if required, and capable of matching closely, directly or indirectly by means of a gutter-like "retainer" or similar placed between the rims, the free perimeter of the body on which they fit together.

This chamber is intended for storing a preferably folded sterile "field", having a diameter of approximately 1 m for example.

These partitions are transpierced right through by a passage, preferably a central passage having a circular cross-section for example, intended for receiving a flexible sleeve, preferably extensible, which is sealed and the interior of which may be made aseptic. This sleeve is intended especially for receiving the pipe 661 and the connections of the sensor-actuators 44 for measuring, for example, the temperatures, pressure, flow rate . . . The end of this sleeve connected and fixed to the lid, is provided with a plug or grommet or the like, permitting a certain amount of relative movement between the sleeve and the pipe and connections which the sleeve encloses and which exit therefrom; the opposite end, the free end so to speak, of this sleeve is provided with another plug, grommet or the like of a type which relatively immobilises the sleeve and the pipe and connections which exit therefrom.

For this alternative embodiment, in the initial state, the body 630 and the lid 632 are separated and independently packaged, at least partially, in order for each to form an autonomous aseptic entity. In order to do this, the perimeter of the body 630 intended for receiving the lid is hermetically closed by a known appropriate frangible sealing membrane, as well as the nozzle 631 and, if necessary, the other nozzles 610, 620 for example. Likewise, the dish of the double-bottom lid, which will be rotated towards the body of the vessel and which serves to house catheters, probes, cannulae, sensors, is hermetically closed by a similar frangible sealing membrane.

Implementation of this alternative form is carried out as indicated hereinbelow.

Having removed the organ from the donor, the membrane which closes the dish of the lid is ruptured in order to release the catheters, probes, cannulae and sensors which are housed therein and they are placed on the organ. Subsequently the sterile field is deployed and thus serves to protect the organ. The membrane which closes the body of the vessel is then ruptured and the lid together with the organ is placed on the body. If required, the lid is sealed on the body with the aid of an appropriate sterile adhesive strip. The organ is thus placed in a hermetic and sterile volume which may be connected especially to the pumping unit and to the control unit.

As is shown in the drawing, the vessel 63 is held in the holder 600 by virtue of a bracket 601 or the like. The reservoir bag 61 is, for example, suspended from or otherwise fixed to the holder, for example with the aid of support brackets as illustrated while the collector bag 62 rests or is otherwise held on the bottom of this holder (not shown in order not to burden the drawing).

The dispensing unit 65 is for example a catheter or the like intended to be implanted in the organ to be grafted, for example approximately either in a horizontal position or in a vertical position. This catheter, for example of any known type must be of an "atraumatic" and "undisplantable" type in such a manner that when the pipe 661 is connected to the organ, the latter cannot contuse and/or become separated from this catheter during transporting because of possible shocks and vibrations.

Preferably the reservoir bag 61, the collector bag 62, the transporting vessel 63, the suspension device 64, the dispensing element 65 and the pipework 66 as well as, optionally, the support holder 600 are of the disposable and single-use type. Thus the conditions of asepsis may be strictly observed as these consumable constituents are only used once and therefore do not have to be cleaned and sterilised with a view to a new utilisation. To manufacture them, standard materials in medical use, suitably selected and appropriate to each of them, are employed.

It is clear that if the anticipated duration of the transporting is significant, and longer than the specific capacities of the reservoir bag 61 and of the collector bag 62, either the latter are exchanged or else the reservoir bag replenished and/or the collector bag emptied, and this being done of course by respecting and preserving the strict conditions of asepsis.

Among the sensors 44 figure probes which enable the temperature $\theta$ to be measured, at one or more points, in the enclosure and also the organ, such as the ventricles and the septum of the organ to be grafted, as well as the temperature of the fluid for physiological use, which probes make it possible to measure the flow rate d and the pressure P of the fluid as well as the values of pH and other parameters sought by the medical teams and required for their information as, for example the partial pressures of gases such as $CO_2$ and $O_2$.

The container according to the invention is suitable for operating in ambient temperatures between, for example, approximately $-10°$ C. and $+38°$ C. while holding a temperature within the thermally insulated enclosure between approximately 4° C. and 12° C. and this is within $\pm 1.5°$ C.

The electrical power source, for example an internal 12 volt battery, makes it possible to have total and absolute autonomy of operation for two hours.

The control unit makes it possible to monitor and record besides time, the intentional or accidental opening and closing of the container, the outside temperature, the temperature in the thermally insulated enclosure, the temperature of the organ to be grafted and of the liquid for physiological use, the flow rate and pressure of the liquid for physiological use, parameters such as the pH, the amount of carbon dioxide, oxygen etc. of the liquid for physiological use, and the electrical supply. It goes without saying that this list is not limiting.

The control unit makes it possible to monitor and record all these data during a period of time of seventy two hours for example. This information may be read and/or retrieved at any instant and stored, if necessary for example for a period of one year, by virtue of the "black box".

The set values may be prerecorded or else recorded on request as a function of the desiderata of the medical teams.

The useful volume of the thermally insulated enclosure is of the order of about forty liters. The reservoir bag has a capacity, for example, between approximately five and ten liters and the collector bag has a capacity, for example, of the order of approximately six to twelve liters while the transporting vessel has a capacity of, for example, between approximately two and four liters.

The entire significance of the container according to the invention which makes it possible to improve the quality and the duration of the preservation whilst being reliable, easy to use, secure and of universal use, is understood.

We claim:

1. Controlled-environment container for preserving and transporting living organs to be transplanted comprising a box with a movable lid delimiting a thermally insulating inner enclosure and outer compartments, a refrigerating unit which is housed partly in one of said compartments and partly in said enclosure and which has means for maintaining a selected specified temperature in said enclosure, a pumping unit which is housed partly in another of said compartments and partly in said enclosure and which includes means for supplying at least one organ to be placed in said enclosure with a fluid for physiological use at a selected specified pressure and flow rate, a control means which is connected to said refrigerating and pumping units and which is adapted to operate said refrigerating and pumping units and monitor their assigned operations, and an electrical power source which is connected to said refrigerating and pumping units and which supplies power to said refrigerating and pumping units, and wherein said container further comprises a disposable aseptic detachable transporting assembly provided with: a reservoir means comprising a bag adapted to contain said fluid; a collector means comprising a bag adapted to collect fluid which has been supplied to said organ; a transporting means adapted to receive said organ and including means for receiving a suspension device in order to hold said organ and a dispensing means adapted to supply said organ with said fluid; and pipework connecting said reservoir means and said dispensing means by passing via said pumping unit and connecting said transporting means and said collector bag.

2. Container according to claim 1, wherein said transporting means comprises a body with a nozzle for receiving said pipework, and a lid with openings for the passage of said suspension device and for the passage of said pipework going to said dispensing element.

3. Container according to claim 1, wherein said suspension device comprises a gripper.

4. Container according to claims 2, wherein said openings comprise an approximately rectangular slot which emerges in the periphery of the lid and which is intended for receiving in a sliding manner this gripper with the aid of complementary grooves which are provided therein.

5. Container according to claim 2, wherein said openings comprise an approximately semicircular peripheral notch intended for receiving the pipework going to the dispensing element.

6. Container according to claim 2, wherein said suspension device comprises a net and said openings include perforations distributed in a circle in the vicinity of the periphery of the lid in order to receive said net.

7. Container according to claim 1, wherein said pumping unit comprises a peristaltic pump head with a rotor having at least one roller and with a circular guide enveloping a portion of an outer circular path of said at least one roller and wherein said pipework connecting said reservoir means and said dispensing means comprises a pipe with a flexible tubing inserted against said guide in order to be pressed therein by said at least one roller.

8. Container according to claim 1, wherein said dispensing element is a "undisplantable" non-traumatic catheter.

9. Container according to claim 1, wherein said control means comprises a keyboard, a display screen, electronic circuits for processing information with memories, logic functions and comparison functions, sensor-actuators in order to transmit information to said electronic circuits and receive therefrom, and electrical connections connecting said display screen, electronic circuits and control means to each other as well as to said refrigerating and pumping units and electrical power source.

10. Container according to claim 9, wherein said control means comprises a socket for connection to an external computer.

11. Container according to claim 1, wherein said electrical power source comprises an autonomous internal accumulator, sockets for connection to external generators and voltage-frequency converters in order to supply from external generators power comparable to that of the autonomous internal accumulator.

12. The controlled-environment container of claim 1, wherein said reservoir means and said collector means communicate only through said transporting means, such that fluid is not recirculated from said collector means back to said reservoir means.

* * * * *